(12) United States Patent
Boehm et al.

(10) Patent No.: US 12,364,818 B2
(45) Date of Patent: Jul. 22, 2025

(54) SYRINGE FOR STORING AND DISPENSING A MATERIAL

(71) Applicant: Solventum Intellectual Properties Company, Maplewood, MN (US)

(72) Inventors: Andreas J. Boehm, Reichling (DE); Marc Peuker, Schondorf (DE); Paul J. Homnick, Lake Elmo, MN (US)

(73) Assignee: Solventum Intellectual Properties Company, Maplewood, MN (US)

( * ) Notice: Subject to any disclaimer, the term of this patent is extended or adjusted under 35 U.S.C. 154(b) by 731 days.

(21) Appl. No.: 17/309,290

(22) PCT Filed: Nov. 22, 2019

(86) PCT No.: PCT/IB2019/060072
§ 371 (c)(1),
(2) Date: May 17, 2021

(87) PCT Pub. No.: WO2020/115600
PCT Pub. Date: Jun. 11, 2020

(65) Prior Publication Data
US 2022/0023538 A1 Jan. 27, 2022

(30) Foreign Application Priority Data
Dec. 4, 2018 (EP) .................................. 18209967

(51) Int. Cl.
*A61M 5/19* (2006.01)
*A61C 9/00* (2006.01)

(52) U.S. Cl.
CPC ............. *A61M 5/19* (2013.01); *A61C 9/0026* (2013.01)

(58) Field of Classification Search
CPC ............ A61M 5/19; A61M 2005/2451; A61M 5/31596; A61M 5/20; A61M 5/2448; A61M 5/3129; A61M 5/00; A61M 5/178; A61M 5/2066; A61M 5/24; A61M 5/28; A61M 5/281; A61M 5/284; A61M 5/3134; A61M 5/3135; A61M 5/3294; A61M 2005/1787;
(Continued)

(56) References Cited

U.S. PATENT DOCUMENTS 2,168,686 A   8/1939   Saffir
4,367,737 A   1/1983   Kozam et al.
(Continued)

FOREIGN PATENT DOCUMENTS

EP   521434     1/1993
EP   1602415    12/2005
(Continued)

OTHER PUBLICATIONS

Extended EP Search Report for EP Application No. 18209967.1, mailed on Mar. 28, 2019, 4 pages.
(Continued)

*Primary Examiner* — Kevin C Sirmons
*Assistant Examiner* — Alexandra Lalonde (57) ABSTRACT

A syringe for storing and dispensing a first and a second component of a material. The syringe has a first chamber containing the first component and a second chamber containing the second component. The syringe further has an empty blank chamber that spaces the first and the second chamber from each other.

16 Claims, 4 Drawing Sheets

(58) Field of Classification Search
CPC ...... A61M 2005/3123; A61M 2205/19; A61C 9/0026; A61C 5/62; A61C 5/64; B05B 11/1084; B65D 81/325; A61B 17/00491; A61B 2017/00495

See application file for complete search history.

(56) References Cited

U.S. PATENT DOCUMENTS

| | | | | |
|---|---|---|---|---|
| 4,981,241 | A | * | 1/1991 | Keller ...................... A61C 5/64 |
| | | | | 222/137 |
| 4,989,758 | A | | 2/1991 | Keller |
| 5,240,146 | A | * | 8/1993 | Smedley ............... A61M 5/315 |
| | | | | 604/82 |
| 5,918,772 | A | * | 7/1999 | Keller ............... B05C 17/00509 |
| | | | | 222/145.5 |
| 6,006,948 | A | * | 12/1999 | Auer .................... B65D 81/325 |
| | | | | 222/137 |
| 8,499,976 | B2 | * | 8/2013 | Sogaro ................. B65D 81/325 |
| | | | | 222/153.07 |
| 2009/0218241 | A1 | | 9/2009 | Sogaro |
| 2010/0249829 | A1 | | 9/2010 | Rissman |
| 2014/0158711 | A1 | | 6/2014 | Peuker |
| 2014/0246457 | A1 | | 9/2014 | Miyano et al. |

FOREIGN PATENT DOCUMENTS

| | | | | |
|---|---|---|---|---|
| JP | 2000083967 | A | 3/2000 | |
| JP | 2012-200360 | | 10/2012 | |
| WO | WO 1994-007420 | | 4/1994 | |
| WO | WO-9522941 | A1 * | 8/1995 | ............... A61C 5/64 |
| WO | WO 2007-089948 | | 8/2007 | |

OTHER PUBLICATIONS

International Search Report for PCT International Application No. PCT/IB2019/060072, mailed on Jan. 16, 2020, 4 pages.

* cited by examiner

SYRINGE FOR STORING AND DISPENSING A MATERIAL

CROSS REFERENCE TO RELATED APPLICATIONS

This application is a national stage filing under 35 U.S.C. 371 of PCT/IB2019/060072, filed Nov. 22, 2019, which claims the benefit of European Application No. 18209967.1, filed Dec. 4, 2018, the disclosure of which is incorporated by reference in its/their entirety herein.

FIELD OF THE INVENTION

The invention relates to a syringe for storing and dispensing a first and a second component of a material, and in particular to a syringe that has a first and a second chamber that are separated from each other by an empty blank chamber.

BACKGROUND ART

Dental materials are often provided in the form of two or more components that are stored separate from each other and mixed just before use. Such multi-component dental materials may be provided in a syringe that has two or more chambers for each component. There are a variety of syringes for storing and dispensing dental materials that are provided in the form of two or more components.

To maximize the shelf-life of syringes that are pre-filled with the dental materials it has been proposed to store the components of the dental materials in separated chambers.

For example, U.S. Pat. No. 4,989,758 relates to a double cartridge for two-component compounds. The double cartridge is manufactured in one piece by injection molding and has separate reservoir cylinders. The double cartridge enables the storage of the components therein for a long time, without the occurrence of an undesired premature reaction due to diffusion through the plastic material of the cartridge.

EP 1 602 415 A1 describes a syringe comprising a cartridge, a plug, a piston assembly and a mixing tip for a multi-component paste. The cartridge may be formed by two concentric arranged barrels forming the component chambers for storing the paste components.

Although existing syringes and cartridges provide advantages regarding shelf-life there is still a need for a syringe providing for a maximized shelf-life of the material stored therein and which further helps maximizing the hygiene level during use. Such a syringe further still shall be manufactured at minimized costs.

SUMMARY OF THE INVENTION

The invention relates to a syringe for storing and dispensing a first and a second component of a material, in particular a dental material. The syringe comprises a first chamber and a second chamber. The first chamber contains or can contain the first component, and the second chamber contains or can contain the second component. The syringe further comprises an empty blank chamber that spaces the first and second chamber from each other.

Preferably, the material stored in the syringe can be prepared for use by combining, for example by merging or mixing, the first and second component. The blank chamber is preferably free from any component that is used or required for preparing the material stored in the syringe. More preferably, the blank chamber is empty. The term "empty" thereby means that preferably nothing than eventually air is present in the blank chamber.

The invention is advantageous in that it provides a syringe that allows for storing individual material components separated and spaced from each other. Thus, diffusion between the material components can be minimized or prevented. Further, the invention provides for a syringe that has a cartridge exhibiting a smooth outer cartridge surface. The smooth outer cartridge surface enables quick and efficient cleaning through wiping the cartridge off. Further, the smooth outer cartridge surface minimizes or eliminates any areas that are difficult to access during wiping off. The invention is further advantageous in that it provides a cartridge that can be easily manufactured, for example by injection molding. Thus, the invention helps minimizing the costs for manufacturing the cartridge and helps maximizing the hygiene level during use of the syringe.

In one embodiment the blank chamber and the first and second chamber each extend straight and parallel to a longitudinal axis. Preferably the first and second chamber have a first and second chamber length, respectively, in a dimension parallel to the longitudinal axis. The first and second chamber preferably each extend at a uniform cross-section along the first and second length, respectively. Preferably the first and second chamber each extend at a circular cross-section. Other shapes are possible, for example an oval or D-shaped cross-section.

In an embodiment the blank chamber extends at least over the longer of, or both of, the first and second chamber length. For example, the first and second chamber length may be equal and the blank chamber may have a blank chamber length in a dimension parallel to the longitudinal axis. The blank chamber length may be equal to the first and second chamber length.

In an embodiment the syringe has a cartridge front wall that closes a front end of each of the blank chamber and the first and second chamber. The first chamber preferably has a first dispensing outlet. Further, the second chamber preferably has a second dispensing outlet. The first and second dispensing outlet preferably each extend through the cartridge front wall. The front end of the blank chamber and the front ends of the first and second chamber further form a front end of the cartridge. Accordingly, the front end of the cartridge comprises the first and second dispensing outlet. The first and second dispensing outlet may be part of a receptacle of the cartridge, for receiving a mixer, preferably a static mixer, thereon. Accordingly, the syringe may comprise a mixer, preferably a static mixer. The mixer preferably has an inlet for connecting to the first and second dispensing outlet of the cartridge. Thus, the syringe is configured for advancing the first and second component through the mixer where the first and second component are mixed as they flow through the mixer.

Preferably the blank chamber does not comprise a dispensing outlet. Thus, the blank chamber is prevented from picking up any undesired substances that may be present at the front end of the cartridge, for example during use of the syringe in a patient's mouth.

In one embodiment a first piston is received within the first chamber and closes a rear end of the first chamber. A second piston is preferably received within the second chamber and closes a rear end of the second chamber. The rear end of the first and second chamber are located at or adjacent a rear end of the cartridge. The rear end of the cartridge is located opposite of the front end of the cartridge.

The rear end of the cartridge may have a fingerplate for supporting the cartridge for advancing or expelling the first and second component.

In a further embodiment the syringe has a first plunger arranged adjacent the rear end of the first chamber and a second plunger arranged adjacent the rear end of the second chamber. The first plunger is preferably connected to (or is monolithically formed with) the first piston and the second plunger is connected to (or is monolithically formed with) the second piston. The first and second plunger may be connected to each other. For example, a fingerplate may be arranged at a rear end of each of the first and second plunger. The fingerplate preferably connects the first and second plunger with each other.

In a further embodiment the rear end of the blank chamber is open. Thus, the blank chamber may form a reservoir. The reservoir may be used for accommodating an applicator therein. Such an applicator may be selected from a brush or a spatula for example.

In one embodiment the first chamber is formed by a circumferential first chamber wall and the second chamber is formed by a circumferential second chamber wall. The first and second chamber wall forms an inner surface which may be cylindrical or of an oval or D-shaped cross-section as mentioned above. The syringe may further comprise a first connecting wall connecting the first and second chamber wall. And the syringe may further comprise a second connecting wall connecting the first and second chamber wall. Thus, the first and second chamber wall may be indirectly connected to each other by both, the first and second connecting wall. Further, the first and second chamber wall may not be in direct contact with each other. In particular, preferably the first and second chamber wall do not form any common wall with each other.

Preferably the blank chamber is formed between the first chamber wall, the second chamber wall, the first connecting wall and the second connecting wall. In particular, a portion of the first chamber wall, a portion of the second chamber wall, the first connecting wall and the second connecting wall preferably delimit the blank chamber. Preferably the first and second connecting wall (each) extend tangentially from the first chamber wall. Further, preferably the first and second connecting wall (each) extend tangentially from the second chamber wall. The term "tangentially" means that the first and second connecting wall at a joint to the first chamber wall (or second chamber wall) each extend along a path on a tangent of the first chamber wall (or the second chamber wall). Thus, the first chamber wall, the second chamber wall, the first connecting wall and the second connecting wall transition into each other smoothly, in particular without a groove formed between the first and second chamber wall. This facilitates cleaning and disinfection by wiping, because areas at the cartridge that are difficult to access are minimized.

In one embodiment the first and second connecting wall each have an outer planar surface. The outer planar surface is preferably a surface that faces in a direction away from the syringe, in particular radially away from the longitudinal axis. A cartridge with a planar shape of the first and second connecting wall preferably forms an outer cartridge surface that extends at a racetrack-shaped cross-section.

In a further embodiment the first and second connecting wall each have an outer surface that corresponds to a cylinder segment. The outer surface corresponding to a cylinder segment preferably faces in a direction away from the syringe, in particular radially away from the longitudinal axis. A cylinder segment for the purpose of the present specification extends over less than 360 degrees of a full cylinder. A cartridge in which the first and second connecting wall has an outer surface corresponding to a cylinder segment preferably forms an outer cartridge surface that is cylindrical (meaning having a shape of a full cylinder). Therefore, the first and second connecting wall in combination with a portion of the first chamber wall and a portion of the second chamber wall, may form an outer cartridge surface that is cylindrical.

In one embodiment the syringe has a label. The label is preferably adhered on the outer cartridge surface. Therefore, the label preferably has an adhesive layer provided on one major side of the label. Preferably the adhesive layer is provided over the entire major side of the label. Due to the shape of the outer cartridge surface (with only tangential transitions between the first and second chamber wall and the first and second connecting wall) the label may be adhered on the outer cartridge surface with the entire adhesive layer in contact with the cartridge. In particular the label is preferably nowhere spaced from the cartridge. Therefore, areas between the cartridge and the label that are difficult to access or in which bacteria or undesired substances can accumulate are minimized. Thus, the syringe helps maximizing the hygiene level during use.

In one embodiment the cartridge is monolithically formed, for example injection molded. In particular, the first and second chamber wall as well as the first and second connecting wall are preferably monolithically formed, for example injection molded.

DETAILED DESCRIPTION OF THE INVENTION

Figure 1:
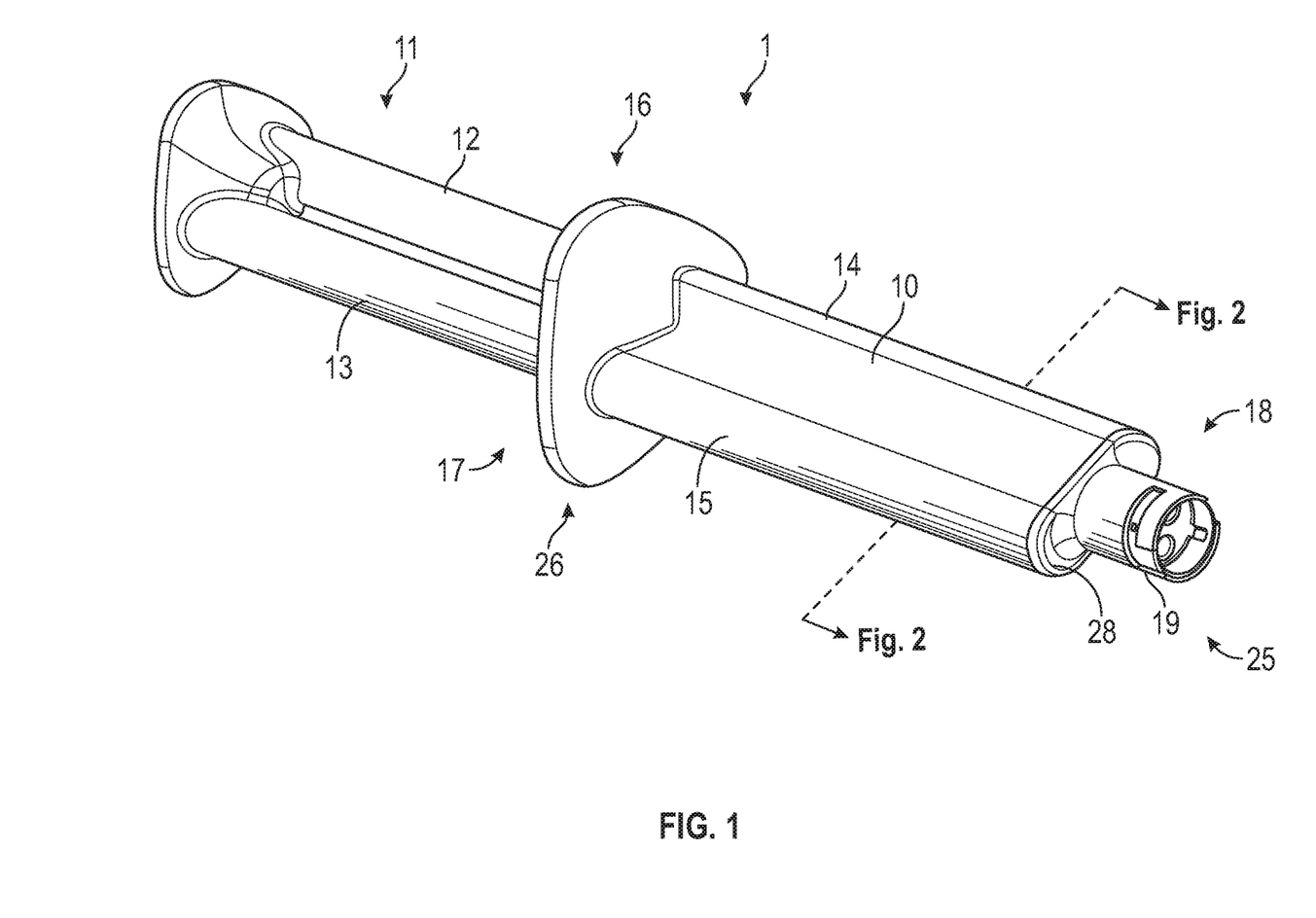
FIG. 1 is a perspective view of a syringe according to an embodiment of the invention.

FIG. 1 shows an exemplary syringe 1 of the invention. The syringe 1 has a cartridge 10 in which a material in the form of a first and a second flowable component can be stored separated from each other. The syringe 1 is configured for expelling the first and second component. Therefore, the syringe 1 comprises a plunger arrangement 11 that has a first and a second plunger 12, 13. The first and second plunger 12, 13 are (partially) received within a first and a second chamber 14, 15, respectively. In particular, a front end 16 of the first plunger 12 is received within the first chamber 14, and a front end 17 of the second plunger 13 is received within the second chamber 15. The front end 16 of the first plunger 12 and the front end 17 of the second plunger 13 in combination form a front end (16, 17) of the plunger arrangement 11. For expelling the first and second component, the plunger arrangement 11 (and thus the first and second plunger 12, 13) are pushed forward in a direction toward a front end 18 of the syringe 1. In the example the syringe 1 at a front end 25 of the cartridge 10 has a receptacle 19 to which a static mixer (see 30 in FIG. 2) can be attached. The first and second component, expelled from the first and second chamber 14, 15, are guided through the static mixer where they are merged and mixed as they flow through the static mixer.

Figure 2:
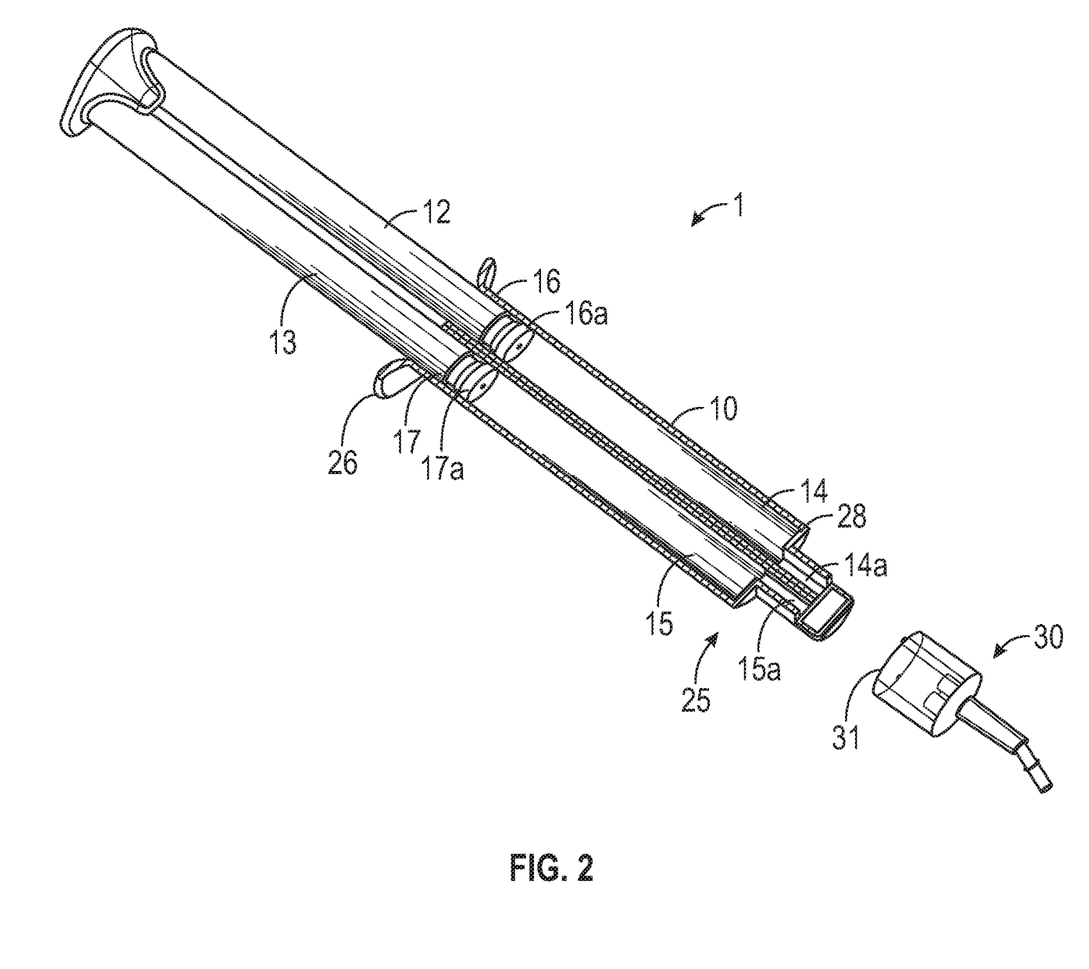
FIG. 2 is a perspective cross-sectional view of the syringe shown in FIG. 1.

As shown in FIG. 2 the first chamber 14 has a first dispensing outlet 14a and the second chamber 15 has a second dispensing outlet 15a. The first and second dispensing outlet 14a, 15a extend through a cartridge front wall 28. The first and second dispensing outlet 14a, 15a are connectable to an inlet 31 (or inlets) of the static mixer 30.

The material (not shown) present in the first and second chamber 14, 15 is preferably a hardenable dental material. The first and second component (stored in the first and second chamber 14, 15, respectively) are flowable and are composed so as to harden or otherwise increase viscosity (typically by chemical reaction) once they are mixed.

The front end 16 of the first plunger 12 and the front end 17 of the second plunger 13 form a first and a second seal 16a, 17a, respectively. The first and second seal 16a, 17a, seal the first and second chamber 14, 15, respectively. In an initial situation in which the cartridge 10 is filled with the first and second component the first and second seal 16a, 17a seal a rear end 26 of the cartridge 10. In the embodiment, the first and second seal 16a, 17a each form a conical lip seal. Such a conical lip seal typically provides for an increased sealing effect in response to an increased pressure during advancing the material or component.

Figure 3:
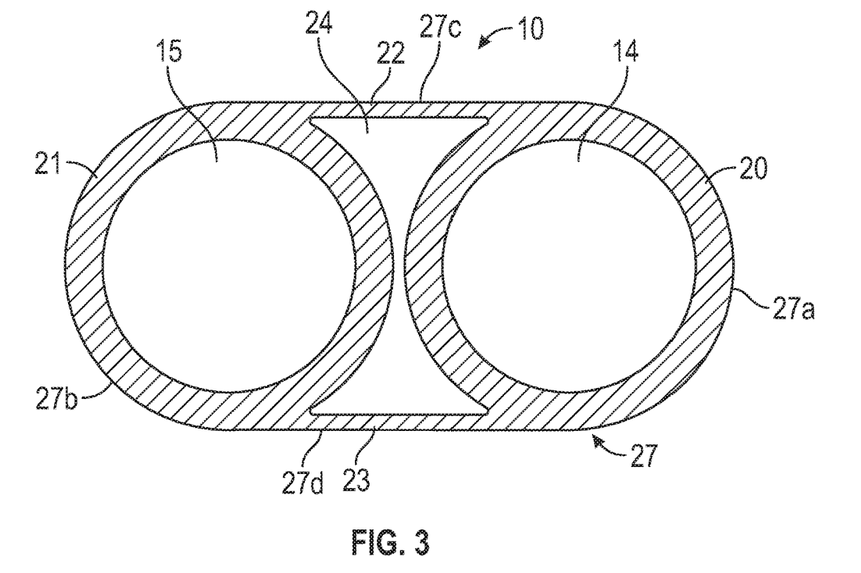
FIG. 3 is a cross-sectional view of a cartridge of a syringe according to an embodiment of the invention.

FIG. 3 shows a cross-section of the cartridge 10. The cartridge 10 forms the first and the second chamber 14, 15 (see also FIGS. 2 and 3). The first chamber 14 is formed by a circumferential first chamber wall 20 and the second chamber 12 is formed by a circumferential second chamber wall 21. In other words, the first and second chamber 14, 15 are formed by circumferentially closed and side-by-side arranged barrels that are not in direct contact with each other.

The cartridge 10 further comprises a first connecting wall 22 that connects the first and second chamber wall 20, 21 with each other. Furthermore, the cartridge 10 comprises a second connecting wall 23 connecting the first and second chamber wall 20, 21 with each other. Thus, the barrels (or the first and second chamber wall 20, 21) are only indirectly connected to each other and are otherwise spaced from each other.

A blank chamber 24 is formed between the first chamber wall 20, the second chamber wall 21, the first connecting wall 22 and the second connecting wall 23. The blank chamber 24 spaces the first and second chamber 14, 15 (and the first and second chamber wall 20, 21) from each other. The blank chamber 24 further is empty, meaning the blank chamber 24 does not contain any material or component thereof that is to be dispensed from the syringe 1.

The first and second chamber wall 20, 21 and the first and second connecting wall 22, 23 in combination provide the cartridge 10 with an outer cartridge surface 27. The outer cartridge surface 27 is thus composed of:
 a first outer cartridge surface portion 27a (provided by the first chamber wall 20),
 a second outer cartridge surface portion 27b (provided by the second chamber wall 21),
 a third outer cartridge surface portion 27c (provided by the first connecting wall 22) and
 a fourth outer cartridge surface portion 27d (provided by the second connecting wall 23).

The first and the fourth outer surface portion 27a, 27d transition into each other based on the same tangent on the first and fourth outer surface portion 27a, 27d. Further, the fourth and the second outer surface portion 27d, 27b transition into each other based on the same tangent on the fourth and second outer surface portion 27d, 27b. The second and the third outer surface portion 27b, 27c transition into each other based on the same tangent on the second and third outer surface portion 27b, 27c. And the third and the first outer surface portion 27c, 27a transition into each other based on the same tangent on the third and first outer surface portion 27c, 27a. Accordingly, the outer cartridge surface 27 is free of sharp transitions, cavities, grooves or edges. This facilitates the cleaning by wiping off the outer cartridge surface 27 with a disinfectant because bacteria are hindered in hiding or being trapped in areas that cannot be easily accessed. In the example the outer cartridge surface 27 extends straight and at a racetrack-shaped cross-section.

Figure 4:
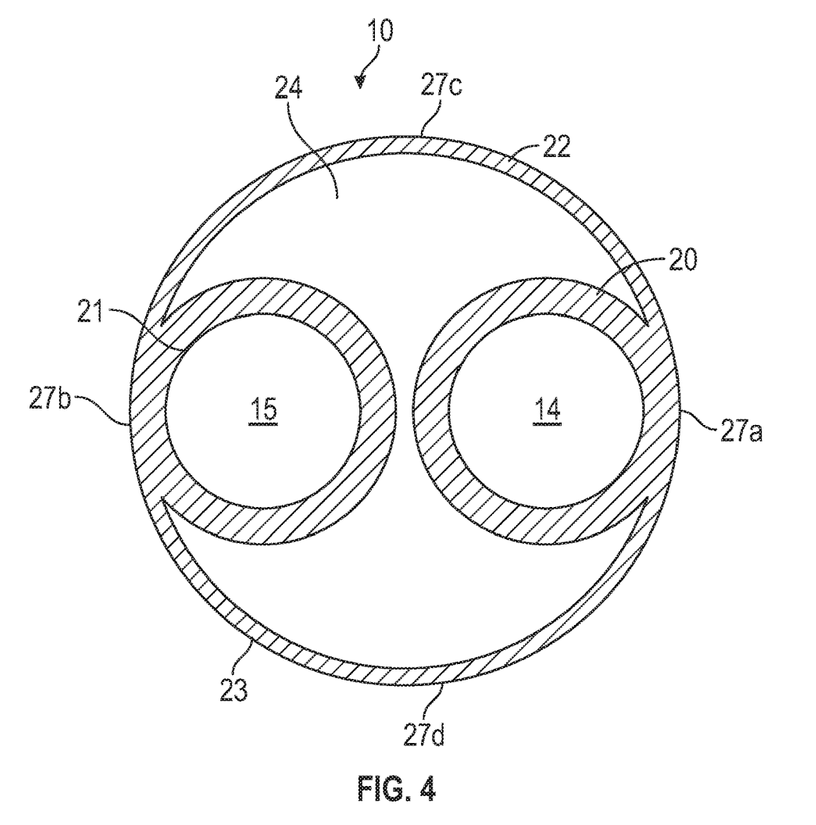
FIG. 4 is a cross-sectional view of a further cartridge of a syringe according to an embodiment of the invention.

FIG. 4 shows an alternative cross-section of the cartridge 10. Again, the cartridge 10 forms the first and the second chamber 14, 15 (see also FIGS. 2, 3 and 4). The first and second chamber 14, 15 are formed by a circumferential first and second chamber wall 20, 12, respectively. In other words, the first and second chamber 14, 15 are formed by circumferentially closed and side-by-side arranged barrels that are not in direct contact with each other.

The cartridge 10 further comprises a first connecting wall 22 that connects the first and second chamber wall 20, 21 with each other. Furthermore, the cartridge 10 comprises a second connecting wall 23 connecting the first and second chamber wall 20, 21 with each other.

A blank chamber 24 is formed between the first chamber wall 20, the second chamber wall 21, the first connecting wall 22 and the second connecting wall 23. The blank chamber 24 spaces the first and second chamber 14, 15 (and the first and second chamber wall 20, 21) from each other. The blank chamber 24 further is empty, meaning the blank chamber 24 does not contain any material or component thereof that is to be dispensed from the syringe 1. However, if desired the blank chamber might be used for storing other items, e.g. an instruction of use or mixing equipment (e.g. static mixer).

The first and second chamber wall 20, 21 and the first and second connecting wall 22, 23 in combination provide the cartridge 10 with an outer cartridge surface 27. The outer cartridge surface 27 is thus composed of:
 a first outer cartridge surface portion 27a (provided by the first chamber wall 20),
 a second outer cartridge surface portion 27b (provided by the second chamber wall 21),
 a third outer cartridge surface portion 27c (provided by the first connecting wall 22) and
 a fourth outer cartridge surface portion 27d (provided by the second connecting wall 23).

The first and the fourth outer surface portion 27a, 27d transition into each other based on the same tangent on the first and fourth outer surface portion 27a, 27d. Further, the fourth and the second outer surface portion 27d, 27b transition into each other based on the same tangent on the fourth and second outer surface portion 27d, 27b. The second and the third outer surface portion 27b, 27c transition into each other based on the same tangent on the second and third outer surface portion 27b, 27c. And the third and the first outer surface portion 27c, 27a transition into each other based on the same tangent on the third and first outer surface portion 27c, 27a. Accordingly, the outer cartridge surface 27 is free of sharp transitions, cavities, grooves or edges. In the example the outer cartridge surface 27 is cylindrical.

Alternative embodiments of these devices could be made with the two inner barrels in direct but tangential contact with each other. The separating wall between them would be the additive thickness of each barrel wall. This would form a syringe with 4 parallel chambers: two side-by-side cylindrical chambers containing paste or other flowable material, which separate two empty chambers whose cross sections are circular horn triangles.

Figure 5:
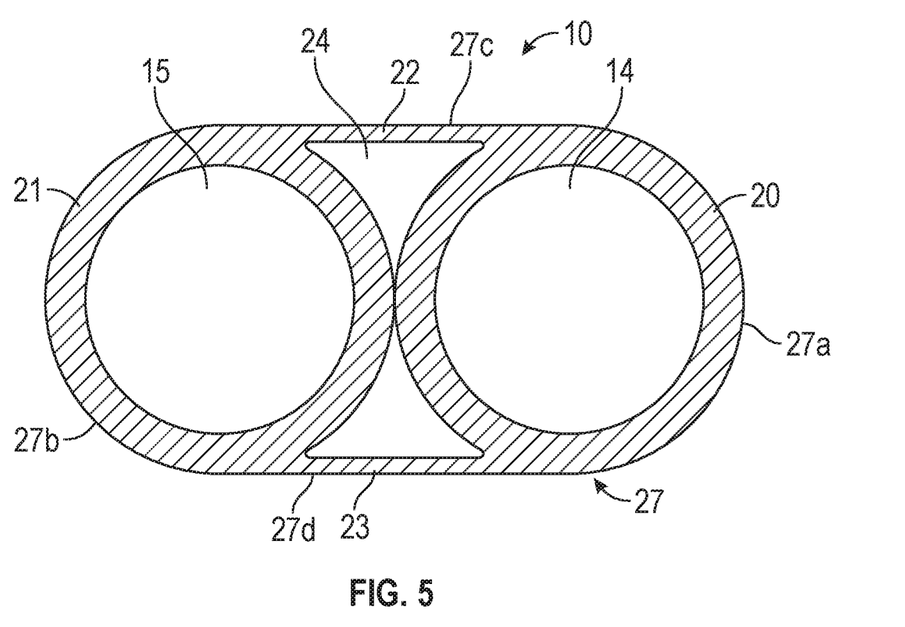
FIG. 5 is a cross-sectional view of a further cartridge of a syringe according to a further embodiment of the invention.

In another embodiment the syringe further comprises a plurality of empty blank chambers that provide spaces between portions of the first and second chamber from each other. In yet another embodiment the empty blank chambers comprise a circular triangle cross-sectional shape (see FIG. 5).

What is claimed is:

1. A syringe for storing and dispensing a first component of a material and a second component of the material, the syringe comprising a first chamber containing the first component of the material and a second chamber containing the second component of the material, wherein the syringe further comprises an empty blank chamber that spaces the first chamber and the second chamber from each other; wherein the syringe further comprises a cartridge front wall that closes a front end of each of the empty blank chamber and the first chamber and the second chamber, wherein the first chamber has a first dispensing outlet and the second chamber has a second dispensing outlet, wherein the first dispensing outlet and the second dispensing outlet each extend through the cartridge front wall, and wherein the empty blank chamber does not comprise a dispensing outlet, wherein the first chamber is formed by a first chamber wall and the second chamber is formed by a second chamber wall, and wherein the syringe further comprises a first connecting wall integrally connecting the first chamber wall and the second chamber wall and a second connecting wall also integrally connecting the first chamber wall and the second chamber wall, wherein the empty blank chamber is formed between the first chamber wall, the second chamber wall, the first connecting wall and the second connecting wall, with the first connecting wall and the second connecting wall on opposing sides of the empty blank chamber and monolithically formed with the first chamber wall and the second chamber wall, wherein the first chamber has a first chamber length and the second chamber has a second chamber length, the first chamber length and the second chamber length each in a dimension parallel to a longitudinal axis, and wherein the first connecting wall and the second connecting wall extend over and at least as long as a longer of the first chamber length and the second chamber length.

2. The syringe of claim 1, wherein the empty blank chamber, the first chamber and the second chamber each extend straight and parallel to the longitudinal axis.

3. The syringe of claim 2, wherein the first chamber and the second chamber each extend at a uniform cross-section along the first chamber length and the second chamber length.

4. The syringe of claim 1, wherein the empty blank chamber has a length that is at least as long as one of or both the first chamber length and the second chamber length.

5. The syringe of claim 1, wherein a first piston is received within the first chamber and closes a rear end of the first chamber, and wherein a second piston is received within the second chamber and closes a rear end of the second chamber.

6. The syringe of claim 5, having a first plunger arranged adjacent the rear end of the first chamber and a second plunger arranged adjacent the rear end of the second chamber, wherein the first plunger is connected to the first piston and the second plunger is connected to the second piston.

7. The syringe of claim 5, wherein a rear end of the empty blank chamber is open.

8. The syringe of claim 1, wherein the first connecting wall and the second connecting wall extend tangentially from the first chamber wall and tangentially from the second chamber wall.

9. The syringe of claim 1, wherein the first connecting wall and the second connecting wall each have an outer planar surface.

10. The syringe of claim 1, wherein the first connecting wall and the second connecting wall each have an outer surface that corresponds to a cylinder segment.

11. The syringe of claim 10, wherein the first connecting wall and the second connecting wall in combination with a portion of the first chamber wall and a portion of the second chamber wall, forms a cylindrical outer cartridge surface.

12. A syringe for storing and dispensing a first component of a material and a second component of the material, the syringe comprising a first chamber containing the first component of the material and a second chamber containing the second component of the material, wherein the syringe further comprises two empty blank chambers; wherein the syringe further comprises a cartridge front wall that closes a front end of each of the two empty blank chambers, and the first chamber, and the second chamber, wherein the first chamber has a first dispensing outlet and the second chamber has a second dispensing outlet, wherein the first dispensing outlet and the second dispensing outlet each extend through the cartridge front wall, and wherein the two empty blank chambers do not comprise a dispensing outlet, wherein the first chamber is formed by a first chamber wall and the second chamber is formed by a second chamber wall, wherein the first chamber wall and the second chamber wall are in direct and tangential contact with each other, and wherein the syringe further comprises a first connecting wall integrally connecting the first chamber wall and the second chamber wall and a second connecting wall also integrally connecting the first chamber wall and the second chamber wall, wherein a first empty blank chamber of the two empty blank chambers is formed between the first chamber wall, the second chamber wall, and the first connecting wall and a second empty blank chamber of the two empty blank chambers is formed between the first chamber wall, the second chamber wall and the second connecting wall, wherein the first chamber has a first chamber length and the second chamber has a second chamber length, the first chamber length and the second chamber length each in a dimension parallel to a longitudinal axis, wherein the first connecting wall and the second connecting wall extend over and at least as long as a longer of the first chamber length and the second chamber length.

13. The syringe of claim 12, wherein the first connecting wall and the second connecting wall on opposing sides of the first empty blank chamber and the second empty blank chamber, are monolithically formed with the first chamber wall and the second chamber wall.

14. The syringe of claim 13, wherein the first empty blank chamber of the two empty blank chambers has a length that is at least as long as one of or both the first chamber length and the second chamber length.

15. The syringe of claim 14, wherein the second empty blank chamber of the two empty blank chambers has a length that is at least as long as one of or both the first chamber length and the second chamber length.

16. The syringe of claim 13, wherein the first empty blank chamber of the two empty blank chambers and the second empty blank chamber of the two empty blank chambers each have a length that is at least as long as a longer of the first chamber length and the second chamber length.

\* \* \* \* \*